US00PP34523P2

(12) United States Plant Patent
de Jong

(10) Patent No.: US PP34,523 P2
(45) Date of Patent: Aug. 30, 2022

(54) ***SYMPHORICARPOS* PLANT NAMED 'KOLMAMOGO'**

(50) Latin Name: ***Symphoricarpos* x *doorenbosii***
Varietal Denomination: KOLMAMOGO

(71) Applicant: Kolster Holding B.V., Boskoop (NL)

(72) Inventor: Jan de Jong, Heelsum (NL)

(73) Assignee: KOLSTER HOLDING B.V., Boskoop (NL)

( * ) Notice: Subject to any disclaimer, the term of this patent is extended or adjusted under 35 U.S.C. 154(b) by 0 days.

(21) Appl. No.: 17/495,892

(22) Filed: Oct. 7, 2021

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Karen M Redden
(74) *Attorney, Agent, or Firm* — Penny J. Aguirre

(57) ABSTRACT

A new cultivar of *Symphoricarpos* plant named 'KOLMAMOGO' that is characterized by its berries that are dark pink to magenta in color, its suitability for use as a cut flower and as a container plant, its mid to early season berry maturation time, and its dense, pink flower clusters.

2 Drawing Sheets

Botanical classification: *Symphoricarpos* x *doorenbosii*.
Variety denomination: 'KOLMAMOGO'.

BACKGROUND OF THE INVENTION

The present invention relates to a new and distinct cultivar of *Symphoricarpos* x *doorenbosii* that will be referred to hereafter by its cultivar name, 'KOLMAMOGO'. The new cultivar represents a new cultivar of snowberry or coralberry that is used as a landscape and container plant.

The new Invention arose from an ongoing controlled breeding program in Heelsum, The Netherlands. The objective was to select a new unique cultivar of *Symphoricarpos* with pink to purple-magenta color berries.

The new cultivar arose from open pollination in August of 2010 of an unpatented proprietary plant in the Inventor's breeding program, 'Kolmagimel', as the female parent. The male parent is therefore unknown. 'KOLMAMOGO' was selected from amongst the resulting seedlings as a single unique plant in October of 2013.

Asexual propagation of the new cultivar was first accomplished under the direction of the Inventor using softwood stem cuttings in November of 2013 in Boskoop, The Netherlands. Asexual propagation by softwood stem cuttings has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'KOLMAMOGO' as a new and unique cultivar of *Symphoricarpos*.

1. 'KOLMAMOGO' exhibits berries that are dark pink to magenta in color.
2. 'KOLMAMOGO' exhibits suitability for use as a cut flower and as a container plant.
3. 'KOLMAMOGO' exhibits a mid to early season berry maturation time.

4. 'KOLMAMOGO' exhibits dense, pink flower clusters.
5. 'KOLMAMOGO' exhibits vertically erect branches.

The female parent of 'KOLMAMOGO' differs from 'KOLMAMOGO' in having berries that are light pink in color and shorter and weaker lateral branches. 'KOLMAMOGO' can be most closely compared to the *Symphoricarpos* cultivars 'Kolmatemta' (not patented) and 'Kolmarufa' (not patented). 'Kolmatemta' and 'Kolmarufa' are both similar to 'KOLMAMOGO' in having similar berry coloration and in being suitable for cut flowers. 'Kolmatemta' differs from 'KOLMAMOGO' in having a different growth habit and a shorter plant height. 'Kolmarufa' differs from 'KOLMAMOGO' in having berries that are lighter in color.

BRIEF DESCRIPTION OF THE DRAWINGS

The accompanying color photographs illustrate the overall appearance and distinct characteristics of the new *Symphoricarpos* 3 years in age as grown outdoors in a 3-gallon container in Dayton, Oreg.

The photograph in FIG. 1 provides a view of the plant habit of 'KOLMAMOGO'.

Figure 1:
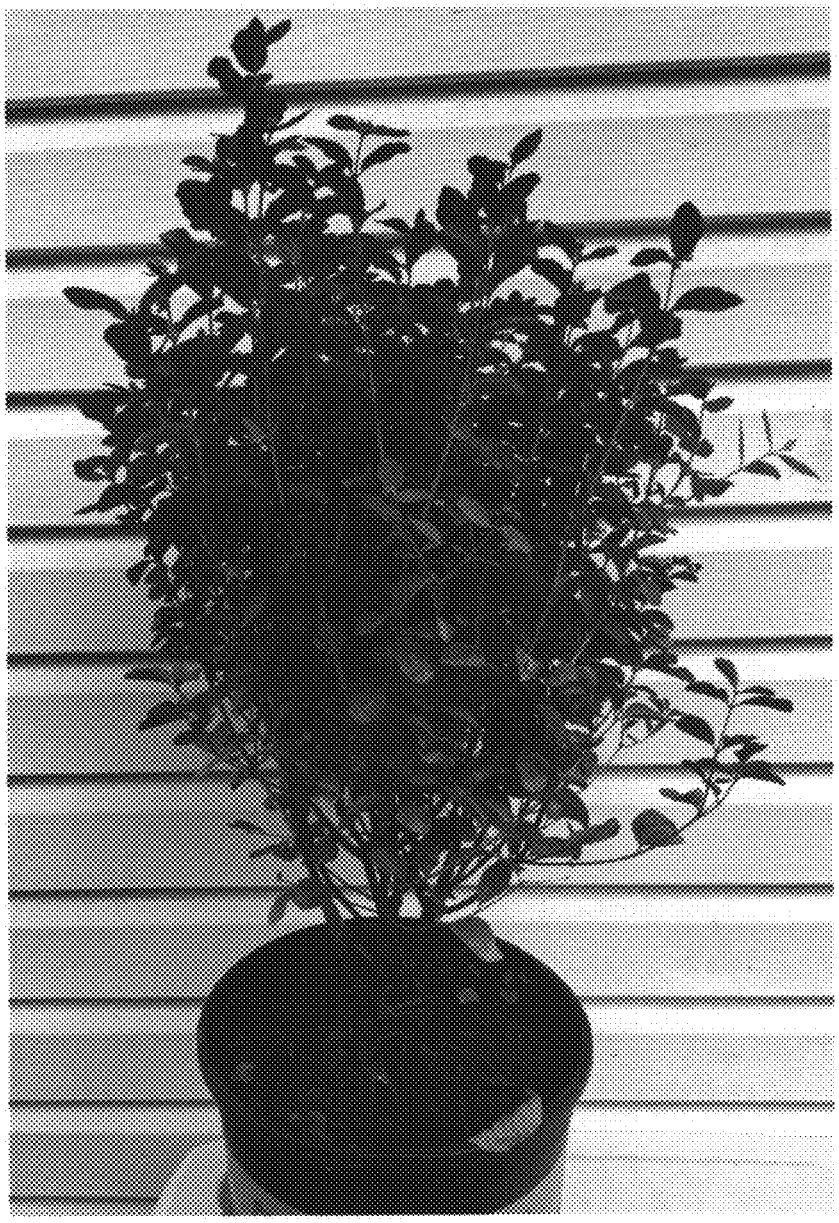
Figure 2:
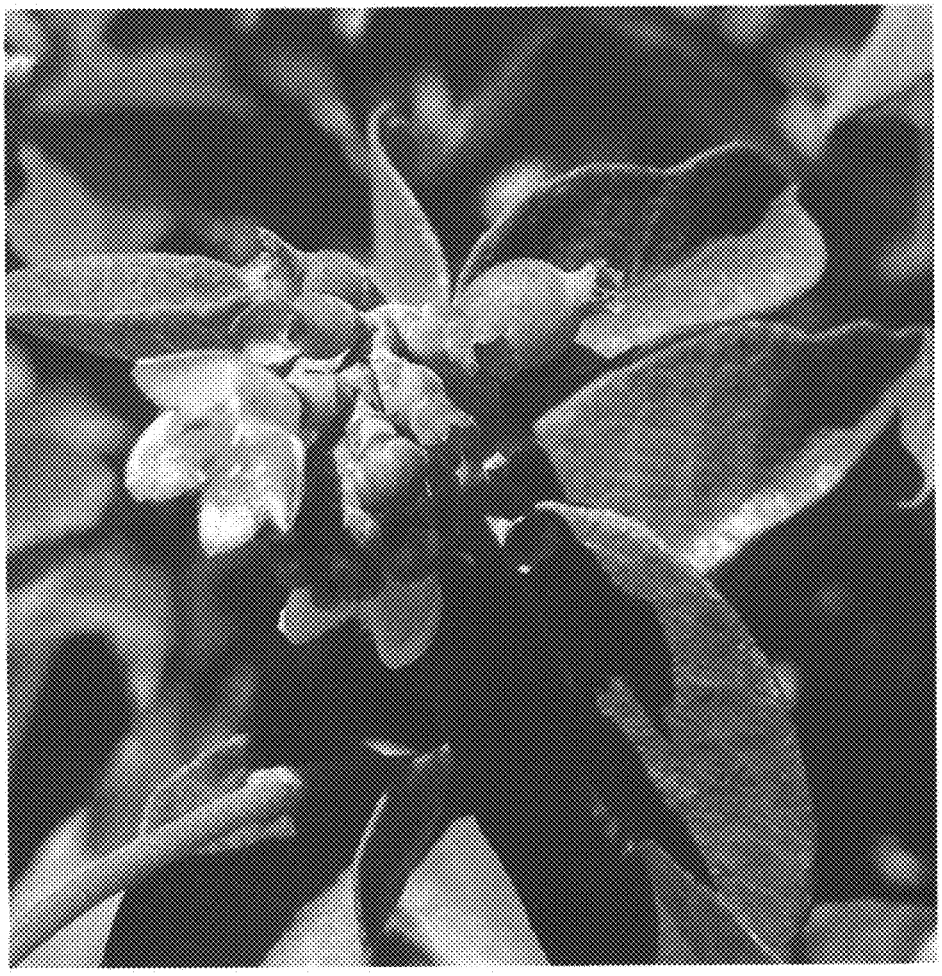

The photograph in FIG. 2 provides a view of an inflorescence of 'KOLMAMOGO'.

The colors in the photographs may differ slightly from the color values cited in the detailed botanical description, which accurately describe the colors of the new *Symphoricarpos*.

DETAILED BOTANICAL DESCRIPTION

The following is a detailed description of 3-year-old plants of the new *Symphoricarpos* as grown outdoors in a 3-gallon container in Dayton, Oreg. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—June to July in The Netherlands.

*Plant habit*.—Compact mound, short stems.

*Plant size*.—An average of 51 cm in height, 44 cm in width, mature plant in the landscape; average of 1.2 m in height, 1 m in width.

*Cold hardiness*.—At least to U.S.D.A. Zone 5.

*Diseases and pests*.—No susceptibility or resistance to diseases or pests has been observed.

*Root description*.—Fibrous, 161C in color.

*Propagation*.—Softwood stem cuttings.

*Root development*.—Roots initiate in about 6 weeks in June, 10 weeks in January and fully root as young plant in about one year, two years for a young plant to produce berries.

*Growth rate*.—Moderately vigorous.

Branch description:

*Branch shape*.—Rounded.

*Stem color*.—New growth; 145A, mature wood; 151A and moderately flushed with 178A, bark 199A and N199B.

*Branch size*.—Main branches; up to 14 cm in length and 5 mm in diameter, lateral branches; an average of 34 cm in length, 3 mm in diameter.

*Branch surface*.—New growth; glabrous and glossy, mature wood is dull and smooth and becoming bark-like as it ages.

*Branching*.—Heavily branched with an average of 7 main branches, average of 7 lateral branches per main branch.

*Internode length*.—Average of 3 cm on lateral branches, 6 cm to 8 cm in main branches.

Foliage description:

*Leaf shape*.—Obtuse to elliptic.

*Leaf division*.—Simple.

*Leaf base*.—Rounded to acute.

*Leaf apex*.—Acute to bluntly acute.

*Leaf fragrance*.—None.

*Leaf venation*.—Pinnate, inconspicuous, colors match leaf surface colors.

*Leaf margins*.—Entire.

*Leaf arrangement*.—Opposite and whorled down branches.

*Leaf attachment*.—Petiolate.

*Leaf surface*.—Glabrous, matte on upper surface and lower surface.

*Leaf size*.—Average of 3 cm in length and 2 cm in width.

*Leaf quantity*.—Average of 30 pair per lateral branch.

*Leaf color*.—Young; both surfaces 145A, mature; upper surface 137A, outer edge of margin 187A, lower surface 137D, outer margin and main vein flushed with 184A.

*Petioles*.—2 to 3 mm in length and 1 mm in width, color; young 137A, mature 137D, flushed with 184A, surface; both surfaces moderately covered with soft, short pubescent hairs 0.5 mm in length, matches surface color.

*Stipules*.—None.

Flower description:

*Flower arrangement and shape*.—Single campanulate flowers arranged in terminal spikes or solitary in leaf axils; freely flowering habit with 2 to 6 flowers per spike.

*Flower aspect*.—Drooping.

*Fragrance*.—None detected.

*Flower longevity*.—Average of 5 days, not persistent.

*Fruit longevity*.—Average of 1 month.

*Flower buds*.—Average of 2 mm in length and 1.5 mm in diameter, oval in shape, matte surface, color; when developing; 59B, mature before burst top to mid-section 60A, base NN155A.

*Inflorescence size*.—Average of 10 cm in length, 8 cm in diameter.

*Flowers*.—Average of 5 mm in length, 6 mm in diameter at top, 3 mm in diameter at base.

*Petals*.—5, arranged in a single whorl, 60% fused into base, 2 mm in length, 3 mm in width, broadly elliptic in shape, acute apex, entire margins, outer surface glabrous, inner surface pubescent, color; outer and inner surface when opening and fully open base, tips and margins NN155C, centers 63B.

*Sepals*.—5, arranged in a single whorl, fused below the apices, average of 0.3 mm in length, 0.5 mm in width at the widest point, acute apex, entire margins, inner and outer surface glabrous, color; inner surface 142B, outer surface N79A.

*Calyx*.—Funnelform, 1 mm in length and diameter.

*Peduncles*.—Strong, 1 mm in width, glabrous and matte surface, color; young 145A, maturing 145A and flushed with 182A, mature 175A.

*Pedicels*.—None, sessile to peduncle.

Reproductive organs:

*Gynoecium*.—Pistils; 1, average of 3 mm in length, stigma; club-shaped, average of 0.5 mm in width, 22A in color, style; average of 2.5 mm in length, NN155C in color, ovary; average of 0.5 mm in diameter, 149A in color.

*Androecium*.—Stamens; 5, 3.5 mm in length, anthers; flattened, narrow oblong in shape, average of 0.5 mm in width, 0.3 mm in depth, 11C in color, filament 3 mm in length, glossy, NN155D in color, surrounded by thin translucent fur-like hairs NN155D in color, pollen; no pollen observed.

*Fruits*.—An average 5 clusters of berries per branch, 12 berries per cluster, fruit size; an average of 5 mm in diameter, 6 mm in depth, spherical in shape, smooth in texture, matte, color; young fruit 142B, mature fruit N78A.

*Seeds*.—Average of length 3 mm, average of 2 mm in diameter, 158A in color.

It is claimed:

1. A new and distinct cultivar of *Symphoricarpos* plant named 'KOLMAMOGO' as herein illustrated and described.

* * * * *